United States Patent [19]

Wolos et al.

[11] Patent Number: 5,470,837
[45] Date of Patent: Nov. 28, 1995

[54] 5'-VINYLHALO-ARISTEROMYCIN/ADENOSINE ANALOGS AND IMMUNOSUPPRESSANTS

[75] Inventors: Jeffrey A. Wolos, Loveland; Niall S. Doherty, West Chester; Esa T. Jarvi, Cincinnati; James R. McCarthy, West Chester, all of Ohio

[73] Assignee: Merrell Dow Pharmaceuticals Inc., Cincinnati, Ohio

[21] Appl. No.: 260,617

[22] Filed: Jun. 16, 1994

Related U.S. Application Data

[63] Continuation of Ser. No. 150,579, Nov. 10, 1993, abandoned, which is a continuation of Ser. No. 900,549, Jun. 18, 1992, abandoned, which is a continuation of Ser. No. 568,579, Aug. 16, 1990, abandoned.

[51] Int. Cl.$^6$ ................................................. A61K 31/70
[52] U.S. Cl. .................. 514/45; 536/27.13; 536/27.14; 536/27.21; 536/27.61; 536/27.63; 536/27.7; 544/254; 544/256; 544/264; 544/278; 548/260; 548/304.4
[58] Field of Search .................... 514/45, 46; 536/27.14

[56] References Cited

U.S. PATENT DOCUMENTS

| | | | |
|---|---|---|---|
| 3,472,837 | 10/1969 | Verheyden et al. | 536/27.14 |
| 4,997,924 | 3/1991 | Jarvi et al. | 536/27.14 |
| 4,997,925 | 3/1991 | Jarvi et al. | 536/27.14 |

FOREIGN PATENT DOCUMENTS

| | | | |
|---|---|---|---|
| 0304889 | 3/1989 | European Pat. Off. | 536/27.14 |

OTHER PUBLICATIONS

Jenkins et al., "4'-Substituted Nucleosides. 2. Synthesis of the Nucleoside Antibiotic Nucleocidin," *J. Am. Chem. Soc.*, 98(11), 3347–3357 (1976).

R. S. Root-Bernstein(I), "AIDS Is More Than HIV: Part I," *Genetic Engineering News*, Sep. 1, 1992, pp. 4–6.

R. S. Root-Bernstein(II), "AIDS Is More Than HIV: Part II," *Genetic Engineering News*, Sep. 15, 1992, pp. 4–5.

Wolos et al.(I), "Immunomodulation by an Inhibitor of S–Adenosyl–L–Homocysteine Hydrolase: Inhibition of in Vitro and in Vivo Allogeneic Responses," *Cellular Immunology*, 149, 402–408 (1993).

Wolos et al.(II), "Immunosuppression Mediated by an Inhibitor of S–Adenosyl–L–Homocysteine Hydrolase," *J. Immunology*, 151(1), 526–534 (1993).

Wolos et al.(III), "Selective Inhibition of T–Cell Activation by and Inhibitor of S–Adenosyl–L–Homocysteine Hydrolase," *J. Immunology*, 150(8), 3264–3273 (1993).

Wolos et al.(IV), "Suppression of in Vitro and in Vivo T Cell Function by an Inhibitor of S–Adenosyl Homocysteine Hydrolase," Abstract No. 0–427, *Keystone Symposia on Molecular & Cellular Biology, 20th Annual Meeting*, published in *J. Cellular Biochem.*, Supplement 15E, 1991, Wiley–Liss (publisher), see p. 187.

Schmidt et al., "3–Deazaadenosine–An Inhibitor of Interleukin 1 Production by Human Peripheral Blood Monocytes," *Int. J. Immunopharmac.*, 12(1), 89–97 (1990).

Puck et al., "Regulatory Interactions Governing the Proliferation of T Cell Subsets Stimulated by Pokeweed Mitogen," *J. Immunology*, 132(3), 1106–1112 (1984).

Hom et al., "The Progression of the Inflammation in Established Collagen–Induced Arthritis Can be Altered by Treatments with Immunological of Pharmacological Agents which Inhibit T Cell Activities," *Eur. J. Immunology*, 18, 881–888 (1988).

(List continued on next page.)

*Primary Examiner*—Douglas W. Robinson
*Assistant Examiner*—L. Eric Crane
*Attorney, Agent, or Firm*—T. Helen Payne

[57] ABSTRACT

The present invention relates to a method of effecting immunosuppression in a patient in need thereof comprising administering to said patient an effective immunosuppressive amount of certain 5'-vinylhalo-aristeromycin/adenosine analogs.

8 Claims, No Drawings

OTHER PUBLICATIONS

Burmester et al., "T–Cell Regulation and T Cell Clones in Relation to Synovial Inflammation," published in *Springer Seminars in Immunopathology, vol. 11,* Springer–Verlag publ., 1989, pp. 259–272.

Sinha et al., "Autoimmune Diseases: The Failure of Self Tolerance," *Science,* 248, 1380–1388 (1990).

Henderson et al., "Mediators of Rheumatoid Arthritis," *British Med. Bull.,* 43(2), 415–428 (1987).

Kyle et al., "Beneficial Effect of Monoclonal Antibody to Interleukin 2 Receptor on Activated T Cells in Rheumatoid Arthritis," *Annals Rheumatic Diseases,* 48, 428–429 (1989).

McCarthy et al.,(I), "The Synthesis of Unsaturated Adenine Nucleosides Related of Angustmycin A," *Chem. Comm.,* 1967, 536–537.

Palmer et al., "The Mechanism of Action of S–Adenosylhomocysteinase," *J. Biol. Chem.,* 254(4), 1217–1226 (1979).

Chiang et al., "S–Adenosyl–L–homocysteine Hydrolase: Analogues of S–Adenosyl–L–Homocysteine as Potential Inhibitors," *Molecular Pharmacology,* 13, 939–947 (1977).

Vinegar et al.(I), "Quantitative in vivo Studies of the Acute Actions of Anti–inflammatory Drugs in the Rat," *Eur. J. Rheumatol. Inflamm.,* 1, 204–211 (1978).

Vinegar et al. (II), "Some Quantitave Temporal Characteristics of Carrageenin–Induced Pleurisy in the Rat (37397)," *Proc. Soc. Exp. Biol. Med.,* 143, 711–714 (1973).

Medhi et al., "The Mechanism of Inhibition of S–Adenosyl–L–Homocysteine Hydrolase by Fluorine–Containing Adenosine Analogs," *J. Enzyme Inhibitors,* 4, 1–13 (1990).

Jarvi et al. (IV), "4',5'–Unsaturated 5'–Halogenated Nucleosides. Mechanism–Based and Competitive inhibitors of S–Adenosyl–L–homocysteine Hydorlase," *J. Med. Chem.,* 34, 647–656 (1991).

McCarthy et al.(II), "4',5'–Unsaturated 5'–Fluoroadenosines Nucleosides: Potent Mechanism Based Inhibitors of S–Adenolyl–L–homocysteine Hydrolase," *J. Am. Chem. Soc.,* 111, 1127–1128 (1989).

5'-VINYLHALO-ARISTEROMYCIN/ADENOSINE ANALOGS AND IMMUNOSUPPRESSANTS

CROSS-REFERENCE TO RELATED APPLICATION

This is a continuation of application Ser. No. 08/150,579, filed Nov. 10, 1993, abandoned, which is a continuation of application Ser. No. 07/900,549, filed Jun. 18, 1992, now abandoned; which is a continuation of application Ser. No. 07/568,579, filed Aug. 16, 1990, now abandoned, which is herein incorporated by reference.

FIELD OF THE INVENTION

This invention relates to the method of use of certain 5'-vinylhalo-aristeromycin/adenosine analogs which are useful as immunosuppressants.

BACKGROUND OF THE INVENTION

Immunity is concerned with the recognition and disposal of foreign antigenic material which is present in the body. Typically the antigens are in the form of particulate matter (i.e., cells, bacteria, etc.) or large protein or polysaccharide molecules which are recognized by the immune system as being "non-self", i.e., detectably different or foreign from the animals own constituents. Potential antigens can be a variety of substances, often proteins, which are most frequently located on the outer surfaces of cells. For example, potential antigens can be found on pollen grains, tissue grafts, animal parasites, viruses, and bacteria. Once the antigenic material is recognized as "non-self" by the immune system, natural (non-specific) and/or adaptive immune responses can be initiated and maintained by the action of specific immune cells, antibodies and the complement system. Under certain conditions, including in certain disease states, an animal's immune system will recognize its own constituents as "nonself" and initiate an immune response against "self" material.

An immune response can be carried out by the immune system by means of natural or adaptive mechanisms, each of which are composed of both cell-mediated and humoral elements. Natural mechanisms for immune response refer to those mechanisms involved in essentially non-specific immune reactions which involve the complement system and myeloid cells alone, such as macrophages, mast cells and polymorphonuclear leukocytes (PMN), in reacting to certain bacteria, viruses, tissue damage and other antigens. These natural mechanisms provide what is referred to as natural immunity. Adaptive mechanisms for immune response refer to those mechanisms which are mediated by lymphocytes (T and B cells) and antibodies which can respond selectively to thousands of different materials recognized as "non-self". These adaptive mechanisms provide what is referred to as adaptive immunity and lead to a specific memory and a permanently altered pattern of response in adaptation to the animal's own environment. Adaptive immunity can be provided by the lymphocytes and antibodies alone or, more commonly, can be provided by the interaction of lymphocytes and antibodies with the complement system and myeloid cells of the natural mechanisms of immunity. The antibodies provide the humoral element of the adaptive immune response and the T-cells provide the cell-mediated element of the adaptive immune response.

Natural mechanisms of immune response involve phagocytosis by macrophages and PMN whereby foreign material or antigen is engulfed and disposed of by these cells. In addition, macrophages can kill some foreign cells through its cytotoxic effects. The complement system which is also involved in natural immunity is made up of various peptides and enzymes which can attach to foreign material or antigen and thereby promote phagocytosis by macrophages and PMN, or enable cell lysis or inflammatory effects to take place.

Adaptive mechanisms of immune response involve the actions against specific antigens of antibody secreted by B-lymphocytes (or B-cells) as well as the actions of various T-lymphocytes (or T-cells) on a specific antigen, on B-cells, on other T-cells and on macrophages.

Antibodies, which are responsible for the humoral aspect of adaptive immunity, are serum globulins secreted by B-cells with a wide range of specificities for different antigens. Antibodies are secreted in response to the recognition of specific antigens and provide a variety of protective responses. Antibodies can bind to and neutralize bacterial toxins and can bind to the surface of viruses, bacteria, or other cells recognized as "non-self" and thus promote phagocytosis by PMN and macrophages. In addition, antibodies can activate the complement system which further augments the immune response against the specific antigen.

Lymphocytes are small cells found in the blood which circulate from the blood, through the tissues, and back to the blood via the lymph system. There are two major subpopulations of lymphocytes called B-cells and T-cells. B-cells and T-cells are both derived from the same lymphoid stem cell with the B-cells differentiating in the bone marrow and the T-cells differentiating in the thymus. The lymphocytes possess certain restricted receptors which permit each cell to respond to a specific antigen. This provides the basis for the specificity of the adaptive immune response. In addition, lymphocytes have a relatively long lifespan and have the ability to proliferate clonally upon receiving the proper signal. This property provides the basis for the memory aspect of the adaptive immune response.

B-cells are the lymphocytes responsible for the humoral aspect of adaptive immunity. In response to recognition of a specific foreign antigen, a B-cell will secrete a specific antibody which binds to that specific antigen. The antibody neutralizes the antigen, in the case of toxins, or promotes phagocytosis, in the case of other antigens. Antibodies also are involved in the activation of the complement system which further escalates the immune response toward the invading antigen.

T-cells are the lymphocytes responsible for the cell-mediated aspect of adaptive immunity. There are three major types of T-cells, i.e., the Cytotoxic T-cells, Helper T-cells and the Suppressor T-cells. The Cytotoxic T-cells detects and destroys cells infected with a specific virus antigen. Helper T-cells have a variety of regulatory functions. Helper T-cells, upon identification of a specific antigen, can promote or enhance an antibody response to the antigen by the appropriate B-cell and it can promote or enhance phagocytosis of the antigen by macrophages. Suppressor T-cells have the effect of supressing an immune response directed toward a particular antigen.

The cell-mediated immune response is controlled and monitored by the T-cells through a variety of regulatory messenger compounds secreted by the myeloid cells and the lymphocyte cells. Through the secretion of these regulatory messenger compounds, the T-cells can regulate the proliferation and activation of other immune cells such as B-cells, macrophages, PMN and other T-cells. For example, upon binding a foreign antigen, a macrophage or other antigen presenting cell can secrete interleukin-1 (IL-1) which activates the Helper T-cells. T-cells in turn secrete certain lymphokines, including interleukin-2 (IL-2) and γ-interferon, each of which have a variety of regulatory effects in the cell-mediated immune response. Lymphokines are a large family of molecules produced by T-cells (and sometimes B-cells) including IL-2, which promotes the clonal proliferation of T-cells;

MAF or macrophage activation factor, which increases many macrophage functions including phagocytosis, intracellular killing and secretion of various cytotoxic factors;

NAF or neutrophil activation factor, which increases many functions of the PMN including phagocytosis;

MIF or macrophage migration factor, which by restricting the movement of macrophages, concentrates them in the vicinity of the T-cell;

γ-interferon, which is produced by the activated T-cell and is capable of producing a wide range of effects on many cells including inhibition of virus replication, induction of expression of class II histocompatibility molecules allowing these cells to become active in antigen binding and presentation, activation of macrophages, inhibition of cell growth, induction of differentiation of a number of myeloid cell lines.

Activated macrophages and PMNs, which provide an enhanced immune response as part of the cell-mediated adaptive immunity, are characterized as having increased production of reactive oxygen intermediates. This increased production of reactive oxygen intermediates, or respiratory burst, is known as "priming". Certain lymphokines, such as γ-interferon, trigger this respiratory burst of reactive oxygen intermediates in macrophages and PMNs. Thus, lymphokines, such as γ-interferon, which are secreted by the T-cells provide an activation of these macrophages and PMNs which results in an enhanced cell-mediated immune response.

The immune response can provide an immediate or a delayed type of response. Delayed-type hypersensitivity is an inflammatory reaction which occurs in immune reactive patients within 24–48 hours after challenge with antigen and is the result primarily of a cell-mediated immune response. In contrast, immediate-type hypersensitivity, such as that seen in anaphylactic or Arthus reactions, is an inflammatory reaction which occurs in immune reactive patients within minutes to a few hours after challenge with antigen and is the result primarily of humoral or antibody-mediated immune response.

The ability of the immune system, and in particular the cell-mediated immune system, to discriminate between "self" and "non-self" antigens is vital to the functioning of the immune system as a specific defense against invading microorganisms. "Non-self" antigens are those antigens on substances in the body which are detectably different or foreign from the animals own constituents and "self" antigens are those antigens which are not detectably different or foreign from the animals own constituents. Although the immune response is a major defense against foreign substances which can cause disease, it cannot distinguish between helpful and harmful foreign substances and destroys both.

There are certain situations, such as with an allogeneic transplant or in "graft versus host" disease, where it would be extremely useful to suppress the immune response in order to prevent the rejection of helpful foreign tissue or organs. Allogeneic tissues and organs are tissues and organs from a genetically different member of the same species. "Graft versus host" disease occurs where the transplanted tissue, for example in a bone marrow transplant, contains allogeneic T-cells of the donor which cause an immune response against the recipient's own tissues. Although both humoral and cell-mediated immune responses play a role in the rejection of allogeneic tissues and organs, the primary mechanism involved is the cell-mediated immune response. Suppression of the immune response, and in particular, suppression of cell-mediated immune response, would thus be useful in preventing such rejection of allograft tissues and organs. For example, cyclosporin A is currently used as an immunosuppressive agent in the treatment of patients receiving allogeneic transplants and in "graft versus host" disease.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not self" is impaired and the body begins to destroy itself. This can result in an autoimmune diseases such as rheumatoid arthritis, insulin-dependent diabetes mellitus (which involves the autoimmune destruction of the B-cells of the islets of Langerhans which are responsible for the secretion of insulin), certain hemolytic anemias, rheumatic fever, thyroiditis, ulceractive colitis, myesthenia gravis, glomerulonephritis, allergic encephalo-myelitis, continuing nerve and liver destruction which sometimes follows viral hepatitis, multiple sclerosis and systemic lupus erythematosus. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases would be useful in minimizing or eliminating the effects of the disease. Certain of these autoimmune diseases, for example, insulin-dependent diabetes mellitus, multiple sclerosis and rheumatoid arthritis, are characterized as being the result of a cell-mediated autoimmune response and appear to be due to the action of T-cells [See Sinha et al. *Science* 248, 1380 (1990)].

Suppression of the immune response would thus be useful in the treatment of patients suffering from autoimmune diseases. More particularly, suppression of cell-mediated immune response would thus be useful in the treatment of patients suffering from autoimmune diseases due to the action of T-cells such as insulin-dependent diabetes mellitus, multiple sclerosis and rheumatoid arthritis.

SUMMARY OF THE INVENTION

The present invention provides a method of effecting immunosuppression in a patient in need thereof comprising administering to said patient an effective immunosuppressive amount of a compound of the formula (1)

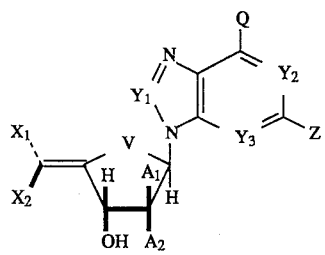
(1)

wherein

V is oxy or methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a CNH2 group, $Y_2$ and $Y_3$ are each independently nitrogen or a CH group, Q is $NH_2$, NHOH, $NHCH_3$, or hydrogen, and Z is hydrogen, halogen, or $NH_2$.

More particularly, the present invention provides a method of suppressing cell-mediated immunity in a patient in need thereof comprising administering to said patient an effective immunosuppressive amount of a compound of formula (1).

DETAILED DESCRIPTION OF THE INVENTION

As used herein the term "halogen" refers to monovalent iodine, bromine, chlorine or fluorine radicals, the term "nitrogen" refers to a trivalent nitrogen radical and the term "CH group" refers to a methylidyne radical.

The aristeromycin/adenosine derivatives of the formula (1) wherein either $X_1$ or $X_2$ is hydrogen can be prepared by utilizing procedures and techniques well known and appreciated by one of ordinary skill in the art. A general synthetic procedure is set forth in Scheme A wherein all substituents, unless otherwise indicated, are as previously defined.

SCHEME A 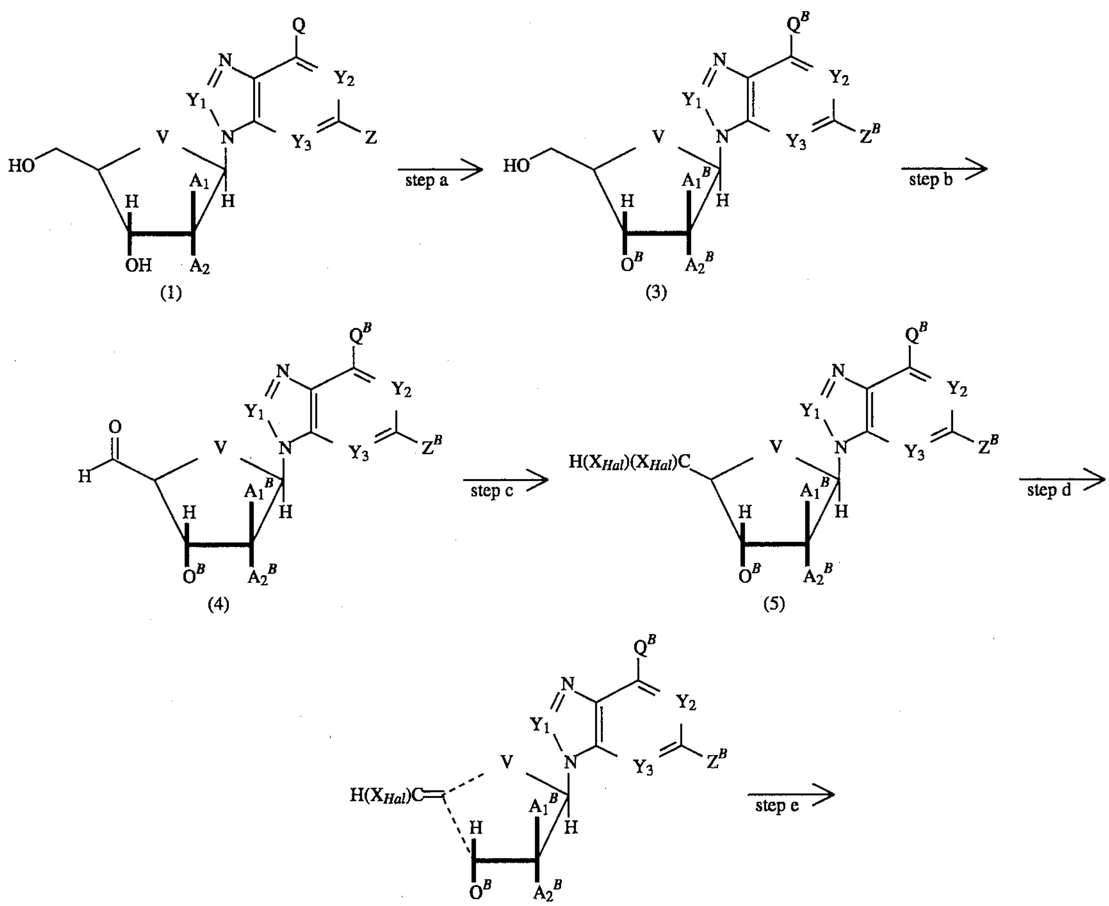 (1) (3) (4) (5) (6)

-continued
SCHEME A

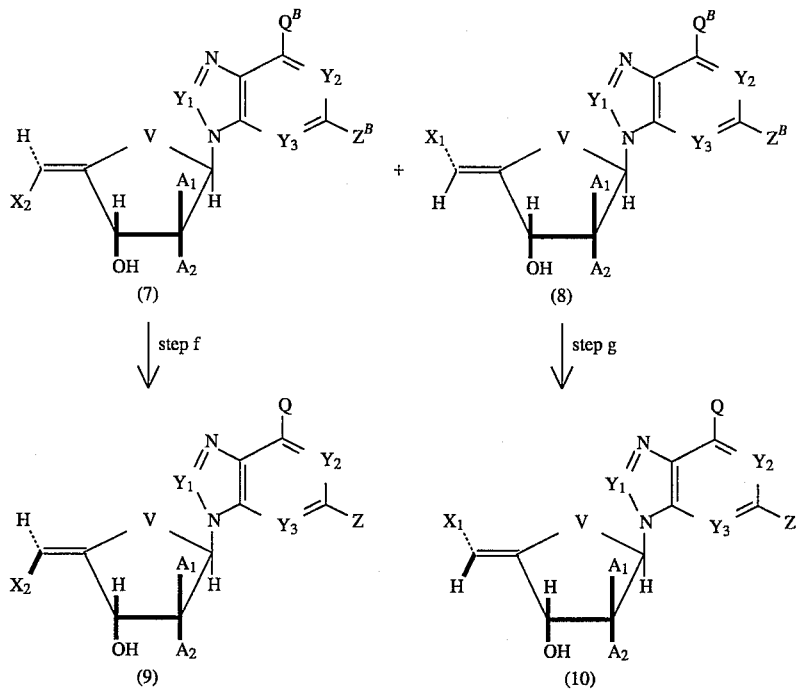

Basically, in step a, reactive hydroxy, amino, or hydroxylamino groups other than the 5'-hydroxy group are blocked with standard blocking agents well known in the art. These blocking groups can be conventional amino protecting groups for Q and Z (wherein Q or Z are $NH_2$) and conventional hydroxy protecting groups for the 3'-hydroxy, for $A_1$ or $A_2$ (wherein $A_1$ or $A_2$ are OH), and for Q (wherein Q is hydroxylamino). $O^B$, $A_1^B$, $A_2^B$, $Q^B$ and $Z^B$ in Scheme A represent the 3'-hydroxy, $A_1$, $A_2$, Q, and Z groups as herein defined blocked with a blocking group where appropriate.

The selection and utilization of particular blocking groups are well known to one of ordinary skill in the art. In general, blocking groups should be selected which adequately protect the amino or hydroxy groups in question during subsequent synthetic steps and which are readily removable under conditions which will not cause degradation of the desired product.

Examples of suitable hydroxy protecting groups are $C_1$–$C_6$ acyl, tetrahydropyranyl, methoxymethyl, methoxyethoxymethyl, t-butyl, benzyl, and triphenylmethyl. The term $C_1$–$C_6$ acyl refers to a saturated acyl radical of one to six carbon atoms of straight, branched, or cyclic configuration. The preferred blocking group for the 3'-hydroxy and for $A_2$ (wherein $A_2$ is hydroxy) is 2',3'-0-isopropylidene formed by reacting the unblocked compound with acetone.

Examples of suitable amino protecting groups are benzoyl, formyl, acetyl, trifluoroacetyl, phthalyl, tosyl, benzenesulfonyl, benzyloxycarbonyl, substituted-benzyloxycarbonyl (e.g., p-chloro,p-bromo, p-nitro, p-methoxy, o-chloro, 2,4-dichloro, and 2,6-dichloro derivatives), t-butyloxycarbonyl (Boc), t-amyloxycarbonyl, isopropyloxycarbonyl, 2-(p-biphenyl)-isopropyloxycarbonyl, allyloxycarbonyl, cyclopentyloxycarbonyl, cyclohexyloxycarbonyl, adamantyloxycarbonyl, phenylthiocarbonyl, and triphenylmethyl. The preferred amino protecting group is the di-benzoyl derivative made by reacting the unblocked compound with benzoyl chloride.

In step b, the appropriately blocked 5'-hydroxy derivative (3) is oxidized to the corresponding aldehyde (4). The preferred oxidizing reagents are dicyclohexylcarbodiimide and methyl phosphonic or dichloroacetic acid and dimethylsulfoxide.

The aldehyde (4) can optionally be derivatized so as to improve the handling characteristics of the compound or to facilitate purification thereof by means of procedures and techniques well known and appreciated in the art. For example, the 5',5'-(N,N'-diphenylethylenediamino) derivative can be prepared by the method of Ranganathan et al. (J. Org. Chem., 39, 290 (1974)].

In step c, the 5',5'-di-halo (i.e., "$X_{(Hal)}(X_{Hal})C$") derivative (5) is formed by reacting the corresponding aldehyde (4) with diethylaminosulfur trihalide or similar halo-substituting reagent. Diethylaminosulfur trihalide is preferred.

In step d, the 5'-di-halo derivative (5) is dehydrohalogenated to form the unsaturated (i.e., "(H)($X_{Hal}$)C") derivative (6). The preferred reagent to effect the dehydrohalogenation is potassium t-butoxide in the presence of dimethylsulfoxide.

In step e, the hydroxy protecting groups are removed according to conventional procedures and techniques well known and appreciated in the art For example, the 2',3'-0-isopropylidene blocking group can be removed by reacting (6) with aqueous trifluroacetic acid. The (Z) and (E) isomers, i.e., (7) and (8), respectively, can conventionally be isolated at this stage of the synthesis by the utilization of conventional isolation techniques as are well known and appreciated in the art. Alternatively, the (Z) and (E) isomers can be isolated after deblocking the amino-protecting groups as described below for steps f and g.

In steps f and g, the amino-protecting groups of the (Z) and (E) isomers, i.e., (7) and (8) respectively, are removed utilizing procedures and techniques well known and appreciated in the art. For example, the benzoyl amino blocking groups can be removed by hydrolysis with ammonia.

Starting materials for use in the general synthetic procedure outlined in Scheme A are readily available to one of ordinary skill in the art. For example, certain starting materials for various compounds of formula (1) are listed in Table 1.

gel column with 4% ethyl acetate/96% dichloromethane. Combine and evaporate the appropriate fractions and collect a yellow oil. Dissolve the oil in ethanol and evaporate three times to yield a solid. Triturate the solid with 50 ml of ethanol and filter. Dry the solid in vacuo to give 2.67 g of the title compound [mp 135–138 degrees Celsius (° C.)].

TABLE 1

Examples of Starting Materials for Scheme A
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | CH | H | $NH_2$ | J. Med. Chem. 25, 626 (1982) |
| O | OH | H | CH | N | N | H | $NH_2$ | Het. Chem. 14, 195 (1977) |
| $CH_2$ | H | OH | CH | N | N | H | $NH_2$ | JACS 88, 3885 (1966) |
| O | H | H | CH | N | N | H | $NH_2$ | 2'-Deoxyadenosine (commercially available) |
| $CH_2$ | H | OH | CH | N | CH | H | $NH_2$ | J. Med. Chem. 25, 626 (1982) |
| O | OH | H | CH | N | N | F | $NH_2$ | JACS 86, 1242 (1964) |
| O | H | OH | CH | CH | N | H | $NH_2$ | Nucleosides & Nucleotides, 1985, p. 625 |
| $CH_2$ | H | OH | CH | N | N | H | $NH_2$ | J. Pharm. Sci. 62, 1252 (1973) |
| $CH_2$ | H | OH | CH | N | N | $NH_2$ | $NH_2$ | J. Med. Chem. 27, 670 (1984) |
| $CH_2$ | H | H | CH | N | N | H | $NH_2$ | J. Med. Chem. 27, 1416 (1984) |
| $CH_2$ | OH | H | CH | N | N | H | $NH_2$ | J. Med. Chem. 20, 612 (1977) |
| $CH_2$ | H | OH | N | N | N | H | $NH_2$ | J. Het. Chem. 10, 601 (1973) |
| $CH_2$ | H | H | N | N | N | $NH_2$ | $NH_2$ | J. Med. Chem. 27, 1416 (1984) |
| $CH_2$ | H | H | N | N | N | H | $NH_2$ | J. Het. Chem. 10, 601 (1973) |
| $CH_2$ | H | OH | N | N | N | $NH_2$ | $NH_2$ | J. Med. Chem. 27, 670 (1984) |
| $CH_2$ | OH | H | N | N | N | $NH_2$ | $NH_2$ | J. Pharm. Sci. 69, 1019 (1980) |
| $CH_2$ | H | OH | CH | CH | N | H | $NH_2$ | Nucleosides Nucleotides 3, 345 (1984) |
| O | H | OH | CH | CH | N | H | $NHCH_3$ | JACS 85, 193 (1963) |
| O | H | OH | CBr | CH | N | H | $NH_2$ | JACS 86, 1242 (1964) |

Additional starting materials can be prepared by the use of methods analogous to those described in Table 1 as well as other conventional methods as are well known and appreciated in the art.

The following example presents a typical synthesis as described by Scheme A. This example is understood to be illustrative only and is not intended to limit the scope of the present invention in any way.

EXAMPLE 1

(Z) and (E)-4',5'-Didehydro-5'-deoxy-5'-fluoroadenosine

Step a: $N^6$-benzoyl-5'-deoxy-2',3'-0-isopropylidene-5',5'-adenosine.

Convert adenosine to its 2',3'-acetonide followed by benzoylation to the N6-benzoyl derivative according to the procedure of Smrt et al. [Coll. Czech. Chem. Comm. 29,224 (1964)].

Step b: $N^6,N^6$-Bis benzoyl-5-deoxy-2',3'-0-isopropylidene 5'-,5'-(N,N'-diphenylethylenediamino)adenosine.

Convert $N^6$-benzoyl-5'-deoxy-2',3'-0-isopropylidene adenosine to $N^6$-benzoyl-5'-deoxy-2',3'-0-isopropylidene-5',5'-(N,N'-diphenylethylenediamino)adenosine according to the procedure of Ranganathan et al. [J. Org. Chem. 39, 290 (1974)]. To 2.96 g of this product in 10 ml of pyridine, cooled in an ice bath, add 1.15 ml (9.9 mmol) of benzoyl chloride. Stir the mixture overnight at room temperature and pour into ice water. Extract the product into 100 ml of chloroform and dry with magnesium sulfate. Evaporate the solution on a rotary evaporator and add toluene. Repeat the evaporation in vacuo, and collect 4.07 g of a yellow foam. Percolate the product through a 40 mm×10 cm flash silica NMR (CDCl$_3$, 90 MHz): δ1.30 (3H, S) 1.50 (3H, S), 3.3–3.7 (4H, m), 4.55 (1H, m), 5.1 (2H, d, J =2), 5.65 (1H, d, J =2), 6.1 (1H, S), 6.3–7.8 21H, M), 8.40 (1H, S).

Step b continued: $N^6,N^6$-Bis benzoyl-2',3'-0-isopropylidene adenosine-5'-aldehyde.

To 2.64 g (3.73 mmol) of $N^6,N^6$-Bis-benzoyl-5'-deoxy-2',3'-0-isopropylidene-5',5'-(N,N -diphenylethylenediamino)adenosine in 370 ml of dichloromethane at 0° C. add a solution of 1.56 g (8.2 mmol) p-toluenesulfonic acid monohydrate in 180 ml of acetone. Stir the mixture for 1.5 hours and filter. Evaporate the filtrate on a rotary evaporator and partition the residue between 200 ml of dichloromethane and water. Dry the dichloromethane solution with magnesium sulfate and evaporate to a foam. Dissolve 2.10 g of the foam in 200 ml of benzene and reflux in a Dean-Stark apparatus for one hour. Evaporate the solvent to give 2.06 g of the title compound. (NMR Spectrum reveals more than 80% of the product as aldehyde.)

NMR (CDCl$_3$, 90 MHz): δ1.40 (3H, S) 1.70 (3H, S), 4.65 (1H, S), 5.3 (1H, d, J=7), 5.45 (1H, broad d, J=7), 6.2 (1H, S), 7.2–7.8 (10H, m), 8.10 (1H, S), 8.45 (major) and 8.55 (1H together, two S). 9.3 (1H, S, CHO).

Step c: $N^6,N^6$-Bis-benzoyl-5'-deoxy-5',5'-difluoro-2',3'-0-isopropylideneadenosine.

Chromatograph 6.5 g of $N^6,N^6$-bis-benzoyl-2',3'-0-isopropylideneadenosine- 5'-aldehyde on a 40 mm×7 cm flash silica gel column with 15% ethyl acetate/85% dichloromethane solvent. Combine and evaporate all fractions with UV—active material on Thin Layer Chromatography (TLC) to give 5.2 g of a foam. Reflux the foam in 200 ml of benzene for 2 hours and then evaporate and dry in vacuo to give 4.65 g of purified $N^6,N^6$-bis-benzoyl- 2',3'-0-isopropylideneadenosine-5'-aldehyde. Dissolve 3.90 g of the 5'-aldehyde in 25 ml of dichloromethane (distilled from calcium hydride) and to this solution add 3.2 ml (3 equivalents) of diethylaminosulfur trifluoride. Stir the mixture for 6 hours. Dilute the mixture with chloroform and pour into 50 ml of stirred saturated aqueous sodium bicarbonate. Extract the product into 400 ml of chloroform and dry with $MgSO_4$. Evaporate the solvent to give 3.60 g of a foam. Percolate the product through a 40 mm×12 cm silica gel flash column with 4% ethyl acetate/96% dichloromethane solvent. Isolate the title compound (738 mg) by TLC ($R_f$ 0.6 with 10% ethyl acetate/90% dichloromethane as solvent).

NMR ($CDCl_3$, 300 MHz): δ1.42 (3H, S) 1.65 (3H, S) 4.42–4.53 (1H, three m), 5.27 (1H, dd, J=2.7, 5.9), 5.39 (1H, dd, J=1.7, 6.0), 5.96 (1H, td, J=55, 4.5), 7.34–7.52 (6H, m), 7.85 (4H, d J=7.2), 8.15 (1H, S), 8.67 (1H, S).

19F-NMR ($CDCl_3$, 282 MHz, ppm from external $CFCl_3$)–54.87 (ddd, J=12.4, 55.2, 299.0) –50.71 (ddd, J=10, 55.2, 299.1)

MS (FAB–XENON) M+1=536

Anal: Calc'd for $C_{27}H_{23}F_2N_5O_5$·C 60.56, H 4.33 Found: C60.26, H.4.44

Step d: $N^6$ Benzoyl-4',5'-didehydro-2',3'-0-isopropylidene-5'-deoxy-5'-fluoroadenosine To 401 mg (0.75 mmol) of crushed $N^6$,$N^6$-Bis-benzoyl-5'-deoxy- 5',5'-difluoro-2',3'-0-isopropylideneadenosine and 335 mg (4 equivalents) of potassium t-butoxide under nitrogen add 2 ml of dimethylsulfoxide (distilled from calcium hydride). Stir the mixture under nitrogen for 21 hours. Quench with 4 ml of saturated ammonium chloride and extract with ethyl acetate to yield 274 mg of yellow oil. Percolate the oil through a 20 mm×15 cm flash column with 30% ethyl acetate/70% dichloromethane. Combine fractions that have two spots close together at $R_f$=0.55 (TLC with ethyl acetate as solvent). Evaporate these fractions to yield 183 mg of the title compound containing two isomers in a 2:1 ratio.

NMR ($CDCl_3$, 300 MHz): δ1.34 and 1.37 (minor) 3H together two S.), 1.49 (3H, s), 5.35–5.38 (1H, m), 5.56 and 5.90 (1H together; d, J=4 and m, resp.), 6.23 (broad s, minor) and 6.25 (1H together), 6.43 (d, J=74, major) and 6.81 (d, J=77; 1H together), 7.39–7.98 (6H, m), 8.646 (major) and 8.653 (minor; two s, 1H together), 9.05 (1H, broad, NH)

NMR $^{19}F$, 282 MHz, ppm from external $CFCl_3$): δ–158.94 (d, J=74 major), 174.4 (d, J=77, minor) MS: (CI) M+1=412.

Step e: $N^6$-Benzoyl-4',5'-didehydro-5'-deoxy-5'-fluoro adenosine

Dissolve 178 mg of $N^6$-benzoyl-4',5'-didehydro-2',3'-0-isopropylidene- 5'-deoxy-5'-fluoroadenosine (2:1 mixture of isomers) in 2 ml of cold trifluoroacetic acid-water (4:1). Stir the mixture at room temperature for 50 minutes and then evaporate on a rotary evaporator. Chromatograph the residue on a 20 mm×14 cm flash silica gel column with ethyl acetate as the solvent. Combine fractions to give 3 mg of the higher $R_f$ isomer (minor isomer), 58 mg of a mixture of isomers and 83 mg of the lower $R_f$ isomer (major isomer) of the title compound.

NMR ($CD_3OD$, higher $R_f$ isomer, 90 MHz): δ5.1 (2H, m), 6.35 (1H, d, J=6), (1H, D, J=74), 7.5–8.2 (5H, m), 8.63 (1H, s), 8.72 (1H, S).

NMR ($CD_3OD$, major lower $R_f$ isomer, 90 MHz): δ5.00–5.10 (2H, m), 6.37 (1H, d, J=7), 6.48 (1H, a, J=75), 7.54–8.19 (5H, m), 8.53 (1H, s), 8.62 (1H, s).

Step f: (Z)-4',5'-didehydro-5'-deoxy-5'-fluoroadenosine.

Dissolve 83 mg of $N^6$-benzoyl-4',5'-didehydro-5'-deoxy-5'-fluoroadenosine (lower $R_f$ isomer above) in absolute ethanol, evaporate and redissolve in 6 ml of ethanol. Bubble anhydrous ammonia through the ice cooled solution in a 20 mm×12 cm Carius tube. Seal the tube and remove the ice bath. After 14 hours at room temperature, open the tube and evaporate the solution to give 87 mg of crude product. Triturate in 1 ml of methanol and filter off the solid. Dry the product in vacuo to give 20 mg of the title compound (a white powder, softens at 100°–110° C. and melts at 225°–230° C.).

NMR ($CD_3OD$, 300 MHz): δ5.02–5.05 (2H, m), 6.28 (1H, d, J=F), 6.56 (1H, d, J=7.52), 8.21 (1H, s), 8.33 (1H, s).

$^{19}F$-NMR (282 MHz, ppm from external $CFCl_3$): –166.76 (d, J=75.2)

MS: (FAB-XENON) M+1=268

Step g: 4',5'-didehydro-5'-deoxy-5'-fluoroadenosine, with E-isomer as major component.

Dissolve 58 mg of $N^6$-benzoyl-4',5'-didehydro-5'-deoxy-5'-fluoroadenosine (a mixture with the higher $R_f$ isomer being the major isomer) in 5 ml of absolute ethanol, and bubble ammonia through the ice cooled solution in a 20 mm× 12 cm Carius tube for 3 three minutes. Seal the tube and remove the ice bath. After 15 hours at room temperature, open the tube and evaporate the solution. Dissolve the residue in 2 ml of methanol and chromatograph on a 20 mm× 12 cm silica gel flash column. Eluted with ethyl acetate, followed by 10% methanol/90% ethyl acetate. Combine and evaporate fractions containing material at $R_f$ 0.23 (10% methanol/90% ethyl acetate) to yield 30 mg of product. Triturated in 12 mg of methanol and filter off the solid. Dry the product in vacuo to yield 16 mg of the title compound (an off-white powder). NMR indicates a 4:1 mixture of E-isomer to Z-isomer.

$^1H$-NMR (E-isomer $CD_3OD$ 300 MHz): δ5.03–5.07 (2H, m) 6.21 (1H, d, J=6.3), 7.02 (1H, d, J=78.6), 8.20 (1H, s), 8.32 (1H, s).

$^{19}F$-NMR (E-isomer, $CD_3OD$, 282 MHz, ppm from ext. $CFCl_3$): – 182.30 (d, J=78.5).

MS: (CI) mH+=268.

The following specific compounds can be made by procedures analogous to those described above in Example 1:

(Z) or (E)-3-(5-deoxy-5-fluoro-β-D-erythro-pent-4-enofuranosyl)- 5-fluoro-3H-1,2,3-triazolo[4,5-d]pyrimidin-7-amine (Z) or (E)-4',5'-didehydro-5'-deoxy-2,5'-difluoro-adenosine (Z) or (E)-9-(5-deoxy-5-fluoro-β-D-threo-pent-4-enofuranosyl)- 9H-purin-6-amine (Z) or (E)-9(5-deoxy-5-fluoro-β-D-threo-pent-4-enofuranosyl)- 9H-purin-6-amine

[1R-(1α, 2α, 3β, 5E or 5Z)-3-(4-amino-1H-imidazo[4,5c] pyridin-1-yl)-5-(fluoromethylene)-1,2-cyclopentanediol (Z) or (E)-1-(5-deoxy-5-fluoro-β-D-erythro-pent-4-enofuranosyl)- 1H-imidazo[4,5-c]pyridin-4-amine (Z) or (E)-3-(5-deoxy-5-fluoro-β-D-erythro-pent-4-enofuranosyl- 3H-imidazo[4,5-b]pyridin-7-amine (Z) or (E)-9-(5-deoxy-5-fluoro-β-D-erythro-pent-4-enofuranosyl- 9H-purine (Z) or (E)-3-(5-deoxy-5-fluoro-β-D-erythro-pent-4-enofuranosyl)- 1H-pyrazolo[4,3-d]pyrimidin-7-amine (Z) or (E)-2-chloro-4',5'-didehydro-5'-deoxy-5'-fluoroadenosine

[1R-(1α, 2α, 3β, 5E or 5Z)]-3-(6-amino-9H-purin-9-yl)-5(fluoromethylene)-1,2-cyclopentanediol (Z) or (E)-4',5'-didehydro-2',5'-dideoxy-5'-fluoroadenosine (Z) or (E)-2-amino-4',5'-didehydro-5'-deoxy-5'-fluoroadenosine

[1R-(1α, 2α, 3β, 5E or 5Z)]-3-(2,6-diamino-9H-purin-9-yl)-5-(fluoromethylene)-1,2-cyclopentanediol

[1S-(1α, 2E or 2Z, 4α)]-4-(6-amino-9H-purin-9-yl)-5-(fluoromethylene)cyclopentanol

[1R-(1α, 2α, 3β, 5E or 5Z)]-3-(6-amino-9H-purin-9-yl-)-5-(fluoromethylene)-1,2-cyclopentanediol

[1R-(1α, 2α, 3β, 5E or 5Z)]-3-(7-amino-3H-1,2,3-triazolo[4,5-d]pyrimidin-3-yl)-5-(fluoromethylene)-1,2-cyclopentanediol

[1S-(1α, 2E or 2Z, 4B)]-4-(7-amino-3H-1,2,3-triazolo[4,5-d] pyrimidin-3-yl)-2-(fluoromethylene)-cyclopentanol

[1R-(1α,2α, 3β, 5E or 5Z)]-3-(5,7-diamino-3H-1,2,3-triazolo[ 4,5-d]pyrimidin-3-yl)-5-(fluoromethylene)-1,2-cyclopentanediol

[1R-(1α, 2α, 3β, 5E or 5Z)]-3-(5,7-diamino-3H-1,2,3-triazolo[ 4,5-d]pyrimidin-3-yl)-5-(fluoromethylene)-1,2-cyclopentanediol

[1R-(1α, 2α, 3β, 5E or 5Z)-3-(7-amino-3H-imidazo[4,5-b]pyridin-3-yl)-5-(fluoromethylene)-1,2-cyclopentanediol

[1S-(1α, 2E 2Z, 4β)]-4-(5,7-diamino-3H-1,2,3-triazolo[4,5-d] pyrimidin-3-yl)-2-(fluoromethylene)-cyclopentanol (Z) or (E)-3-(5-deoxy-5-fluoro-β-D-erythro-pent-4-enofuranosyl)- 3H-1,2,3-triazolo[4,5-d]pyrimidine-5,7-diamine (Z) or (E)-$N^6$-methyl-4',5'-didehydro-5'-deoxy-5-fluoroadenosine The aristeromycin/adenosine derivatives of the formula (1) wherein $X_1$ and $X_2$ are both halogen can be prepared according to conventional procedures and techniques well known and appreciated by one of ordinary skill in the art. A general synthetic procedures is set forth in Scheme B.

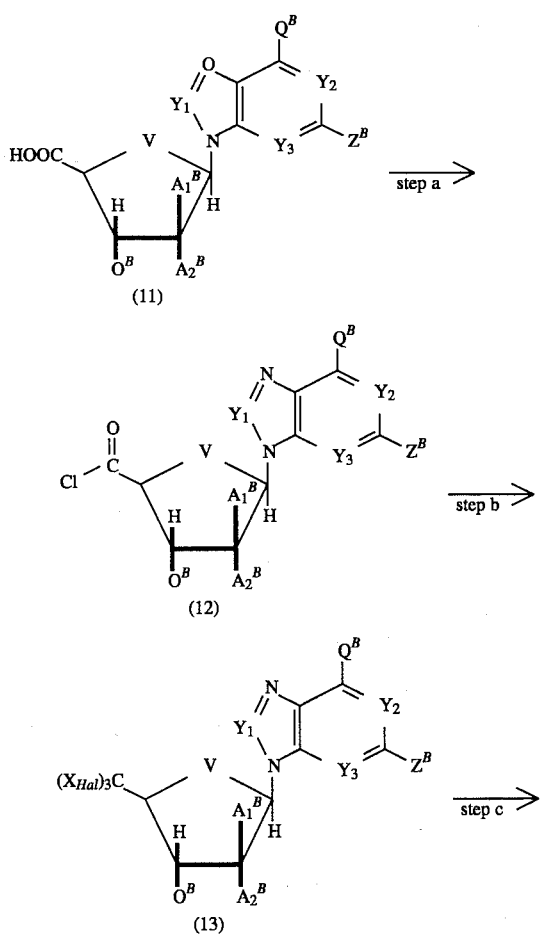

SCHEME B

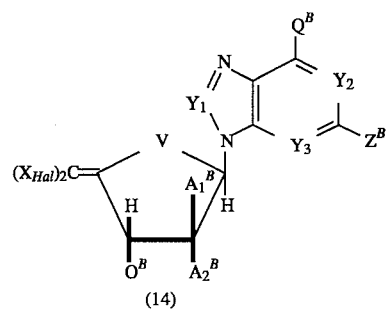

-continued
SCHEME B

In step a, the carboxylic acid derivative (11) in which the appropriate amino and hydroxy groups have been blocked in a manner analogous to that described in Scheme A is converted to the acid chloride (12). The preferred reagent for this reaction is $SOCl_2$. The carboxylic acid derivative (11) can be prepared by oxidation of the corresponding alcohol according to the method of Harmon et al. [Chem. Ind. (London) 1141 (1969)].

The acid chloride derivative (12) is then converted to the tri-halo derivative (13). For example, in order to obtain the trifluoro derivative, (12) can be reacted with phenylsulfur trifluoride in 1,1,2-trichloro-1,2,2-trifluoroethane. In order to obtain the trichloro derivative (13), (12) can be reacted with phosphorus pentachloride or other reagents well known and appreciated in the art.

In step c, the trihalide (i.e., "$(X_{Hal})_3C$") derivative (13) is converted to the 5',5'-di-halo-4',5'-unsaturated derivative (14) in a reaction analogous to that described for Scheme A (step d). The preferred reagent for step c is potassium t-butoxide in dimethylsulfoxide.

The amino and hydroxy blocking groups can then be removed in a manner analogous to that described for Scheme A (steps e, f and g).

Starting materials for use in the general synthetic procedure outlined in Scheme B are readily available to one of ordinary skill in the art. For example, the starting materials for various compounds of formula (1) are listed in Table 2.

TABLE 2

Examples of Starting Materials for Scheme B
Compound of formula (1) wherein

| V | A₁ | A₂ | Y₁ | Y₂ | Y₃ | Z | Q | Source of Starting Material |
|---|----|----|----|----|----|---|---|---|
| O | H | OH | CH | N | CH | H | NH₂ | J. Med. Chem. 25, 626 (1982) |
| O | H | OH | CH | N | N | H | NH₂ | Het. Chem., 14, 195 (1977) aristeromycin |
| O | H | OH | CH | CH | N | H | NH₂ | Nucleosides & Nucleotides, 1985, p. 625 |

Additional starting materials can be prepared by the use of methods analogous to those described in Tables 1 and 2 as well as other conventional methods as are well known and appreciated in the art.

The following example presents a typical synthesis as described by Scheme B. This example is understood to be illustrative only and is not intended to limit the scope of the present invention in any way.

EXAMPLE 2

4',5'-Didehydro-5'-deoxy-5',5'-difluoroadenosine

Steps a and b: 2',3'-0-Isopropylidene-5'-deoxy-5',5',5'-trifluoroadenosine

Combine 3.32 g (0.02 mole) of phenylsulfur trifluoride prepared as described by Sheppard, JACS 84, 3058 (1962)] with 3.25 g (0.01 mole) of the acid chloride of 2',3'-0-isopropylidene adenosine-5'-carboxylic acid [prepared as described in Nucleic Acid Chemistry, Editors: Townsend and Tipson, John Wiley, 1978, p. 701] in 30 ml of 1,1,2-trichloro- 1,2,2-trifluoroethane and heat overnight at 120° C. Add chloroform and pour the mixture into ice water. Extract the mixture with aqueous sodium bicarbonate. Evaporate the organic layer to give the crude product, and chromatograph on flash silica gel with ethyl acetate/methanol to give the title compound.

Step c: 4',5'-didehydro-2',3'-O-isopropylidene-5'-deoxy-5',5'-difluoroadenosine

To 300 mg (0.9 mmole) of 2',3'-0-isopropylidine-5'-deoxy- 5',5',5'-trifluoroadenosine and 410 mg (4 equivalents) of potassium t-butoxide add 2 ml of dimethyl sulfoxide and stir the mixture under nitrogen. Quench with water and extract with ethyl acetate to give the crude product. Chromatograph the crude product on silica gel with ethyl acetate to give the title compound.

De-blocking:   4',5'-didehydro-5'-deoxy-5',5'-difluoro adenosine

Treat 100 mg of 4',5'-didehydro-2',3'-O-isopropylidene-5'-deoxy-5',5'-difluoroadenosine with 2 ml of trifluoroacetic acid/water (4:1) for 1 hour and evaporate the solvent. Chromatograph on silica gel with ethyl acetate/methanol to give 60 mg of the title compound.

The following specific compounds can be made by procedures analogous to those described above in Example 2:
3-(5-deoxy-5,5-difluoro-8-D-erythro-pent-4-enofuranosyl)-5-fluoro- 3H-1,2,3-triazolo[4,5-d]pyrimidin-7-amine,
4',5'-didehydro-5'-deoxy-2,5',5'-trifluoroadenosine
9-(5-deoxy-5,5-difluoro-β-D-threo-pent-4-enofuranosyl)-9H-purin- 6-amine
9(5-deoxy-5,5-difluoro-β -D-threo-pent-4-enofuranosyl)-9H-purin- 6-amine
[1R-(1α, 2α, 3β)-3-(4-amino-1H-imidazo[4,5-c]pyridin-1-yl)- 5-(difluoromethylene)-1,2-cyclopentanediol
1-(5-deoxy-5,5-fluoro-β-D-erythro-pent-4-enofuranosyl)-1H-imidazo[ 4,5-c]pyridin-4-amine
3-(5-deoxy-5,5-difluoro-β-D-erythro-pent-4-enofuranosyl-3H-imidazo[ 4,5-b]pyridin-7-amine
9-(5-deoxy-5,5-difluoro-β-D-erythro-pent-4-enofuranosyl-9H-purine
3-(5-deoxy-5,5-difluoro-β-D-erythro-pent-4-enofuranosyl)-1H-pyrizolo[4,3-d]pyrimidin-7-amine
2-chloro-4',5'-didehydro-5'-deoxy-5',5'-difluoroadenosine
[1R-(1α, 2α, 3β)]-3-(6-amino-9H-purin-9-yl)-5-(difluoromethylene)- 1,2-cyclopentanediol
4',5'-didehydro-2',5'-dideoxy-5',5'-difluoroadenosine
2-amino-4',5'-didehydro-5'-deoxy-5',6'-difluoroadenosine
[1R-(1α, 2α, 3β)-3-(2,6-diamino-9H-purin-9-yl)-5-(difluoromethylene)- 1,2-cyclopentanediol
1S-(1,α2E, 4β)]-4-(6-amino-9H-purin-9-yl)-5-(difluoromethylene)-cyclopentanol
[1R-(1α, 2β, 3β)]-3-(6-amino-9H-purin-9-yl-)-5-(difluoromethylene)- 1,2-cyclopentanediol
[1R-(1α, 2α,3β)]-3-(7-amino-3H-1,2,3-triazolo[4,5-d] pyrimidin-3-yl)-5-(difluoromethylene)-1,2-cyclopentanediol
[1S-(1α, 4, β)]-4-(7-amino-3H-1,2,3-triazolo[4,5-d]pyrimidin- 3-yl-2-(difluoromethylene)-cyclopentanol
[1R-(1α, 2β, 3β)-3-(5,7-diamino-3H-1,2,3-trizolo[4,5-d] pyrinidin-3-yl)-5-(difluoromethylene)-1,2-cyclopentanediol
[1R-(1α, 2α, 3β)]-3-(5,7-diamino-3H-1,2,3-triazolo[4,5-d] pyrimidin-3-yl)-5-(fluoromethylene)-1,2-cyclopentanediol
[1R-(1α, 2α, 3β)]-3-(7-amino-3H-imidazo[4,5-b]pyridin-3-yl)- 5-(fluoromethylene-1,2-cyclopentanediol
[1S-(1α, 4β)]-4-(5,7-diamino-3H-1,2,3-triazolo[4,5-d] pyrimidin-3-yl)-2-(fluoromethylene)-cyclopentanol
3-(5-deoxy-5-fluoro-β-D-erythro-pent-4-enofuranosyl)-3H-1,2,3-triazolo[4,5-d]pyrinidine-5,7-diamine
N⁶-methyl-4',5'-didehydro-5'-deoxy-5'-fluoroadenosine An alternative procedure for preparing adenosine derivatives of the formula (1) wherein one or both of X₁ and X₂ are halogen is set forth in Scheme C. This method involves preparing the adenosyl base and ribosyl moieties separately and then effecting a condensation of the moieties.

SCHEME C

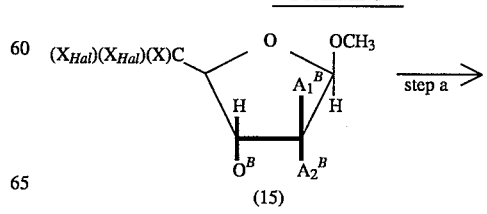

(15)

-continued
SCHEME C

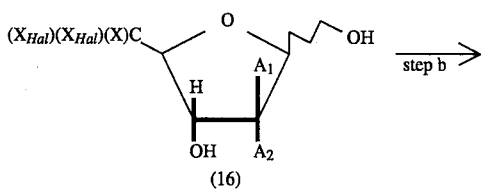

(16)

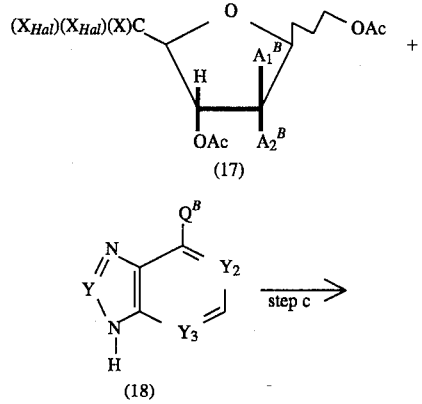

(17)

(18)

-continued
SCHEME C

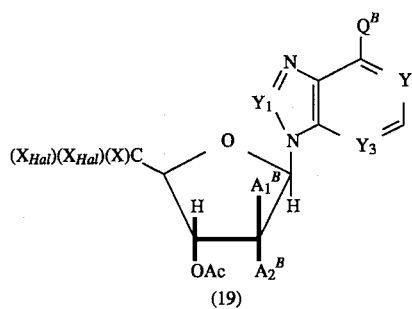

(19)

Di or tri-halo- substituted ribosyl derivatives (15) are prepared according to standard techniques and procedures which are well known and appreciated by those of ordinary skill in the art. For example, these compounds can be prepared by methods analogous to that described by Sharma et al. (Tet. Lett. 1977, 3433) for the preparation of Methyl-5-deoxy-5,5-difluoro-2,3-isopropylideneribose.

These derivatives (15) are hydrolyzed in step a using an acid such as acetic acid. The hydrolyzed derivatives (16) are subsequently converted to the corresponding acetic acid esters (17) in step b by reaction with acetic anhydride in pyridine.

Procedures for making the adenine derivative (18) also involve standard techniques and procedures which are well known and appreciated by those of ordinary skill in the art.

The acetic acid ester (17) can be condensed with the appropriate adenine derivative (18) through a fusion reaction or through a condensation reaction in the presence of bis-trimethylsilylacetamide and a Lewis acid such as trimethylsilyltrifluoromethanesulfonate.

The condensed product (19) can then be de-blocked by hydrolysis and then appropriately blocked as described in Scheme A (step a) and further reacted to provide compounds of formula (1) as described in Scheme A (steps d through g).

Starting materials for use in the general synthetic procedure outlined in Scheme C are readily available to one of ordinary skill in the art. For example, the starting materials for various compounds of the formula (1) are listed in Table 3.

TABLE 3

Examples of Starting Materials for Scheme C
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | N | Cl | $NH_2$ | 2-Chloroadenine and Tet. Lett. 1977, 3433 |
| O | H | OH | CH | N | N | H | $NH_2$ | Adenine |
| $CH_2$ | H | OH | CH | N | CH | H | $NH_2$ | 3-deazaadenine |

Additional starting materials can be prepared by the use of methods analogous to those described in Table 3 as well as other conventional methods as are well known and appreciated in the art.

The following example presents a typical synthesis as described by Scheme C. This example is understood to be illustrative only and is not intended to limit the scope of the present invention in any way.

EXAMPLE 3

$N^6,N^6$-Bisbenzoyl-5'-deoxy-5',5'-difluoro-2',3'-0-isopropylideneadenosine

Steps a and b: 5-deoxy-5,5-difluororibose and 5-deoxy-5,5-difluoro-1,2,3-tri-0-acetylribose Dissolve 1.12 g (5 mmol) of methyl-5-deoxy-5,5-difluoro-2,3-isopropylideneribose (prepared as described by Sharma et al., Tet. Lett. 1977, 3433–3436), in 5 ml of 80% acetic acid and heat at 80° C. for 4 h followed by stirring overnight at room temperature. Evaporate the solvent, add toluene and evaporate again to give 5-deoxy-5,5-difluororibose. To the residue add 2.55 ml (2 mmol) of acetic anhydride and 10 ml of pyridine and stir the mixture was overnight. Subject the mixture to aqueous work-up followed by chromatography on flash silica gel (cyclohexane/dichloromethane) to give 5-deoxy-5,5-difluoro- 1,2,3-tri-o-acetylribose.

Step c: $N^6$-Benzoyl-5'-deoxy-5',6'-difluoro-2', 3'-0-acetyl adenosine

To 1.06 g (4.4 mmol) of N-benzoyl adenine in 30 ml of acetonitrile add 3.2 ml (13 mmol) of bis-trimethylsilyl acetamide. Heat the mixture 0.5 h at reflux. Cool the mixture and add 1.00 g (3.4 mmol) of 5-deoxy-5,5-difluoro- 1,2,3-tri-0-acetylribose, followed by 1.5 ml of trimethylsilyl trifluoromethanesulfonate. Reflux the mixture for 5 hours, cool, and pour into a saturated sodium bicarbonate solution. Extract the product into chloroform, dry and evaporate to give the crude product. Chromatograph on flash silica gel to give the title compound.

De-blocking: 5'-deoxy-5',5'-difluoroadenosine

To 700 mg (1.5 mmol) of $N^6$-benzoyl-5'-deoxy-5',5'-difluoro- 2',3'-0-acetyladenosine in 20 ml of ethanol in a Carius tube add gaseous ammonia while cooling in ice. Seal the tube and allow it to stand overnight. Open the tube and evaporate the solvent. Chromatograph the product on flash silica gel, (ethyl acetate/methanol) to give the title compound.

Blocking: 5'-Deoxy-5',5'-difluoro-2',3'-0-isopropylidene adenosine

To 300 mg (1 mmol) of 5'-deoxy-5',5'-difluoroadenosine in 3 ml of acetone containing 215 mg (1.1 mmol) of p-toluenesulfonic acid monohydrate add 0.65 ml (4 mmol) of ethyl orthoformate while stirring. Stir the mixture for 2 h and then neutralize with dilute ammonium hydroxide. Partition the mixture between water and chloroform and evaporate the chloroform. Chromatograph the product on flash silica gel (ethyl acetate/methanol) to give the title compound.

Blocking: $N^6,N^6$-Bisbenzoyl-5'-deoxy-5',5'-difluoro-2',3'-0-isopropylideneadenosine To 160 mg of 5'-deoxy-5',5'-difluoro-2',3'-0-isopropylidineadenosine in 1 ml of pyridine add 0.17 ml of benzoyl chloride and stir the mixture overnight. Partition the mixture between water and chloroform. Evaporate the chloroform and chromatograph the residue on flash silica gel to give the title compound.

The further work-up of the title compound to yield compounds of formula (9) and (10) is described in Scheme A.

The following specific compounds can be made by procedures analogous to those described in Example 3:

(Z) or (E)-4',5'-didehydro-5'-deoxy-2,5'-difluoro-adenosine
(Z) or (E)-1-(5-deoxy-5-fluoro-β-D-erythro-pent-4-enofuranosyl)- 1H-imidazo[4,5-c]pyridin-4-amine
(Z) or (E)-3-(5-deoxy-5-fluoro-β-D-erythro-pent-4-enofuransyl- 3H-imidazo[4,5-b]pyridin-7-amine
(Z) or (E)-9-(5-deoxy-5-fluoro-β-D-erythro-pent-4-enofuranosyl- 9H-purine
(Z) or (E)-2-chloro-4',5'-didehydro-5'-deoxy-5'-fluoroadenosine
(Z) or (E)-2-amino-4',5'-didehydro-5'-deoxy-5'-fluoroadenosine
(Z) or (E)-$N^6$-methyl-4',5'-didehydro-5'-deoxy-5'-fluoroadenosine.

The aristeromycin/adenosine derivatives of the formula (1), wherein one of $X_1$ and $X_2$ is hydrogen and the other is halogen, can alternatively be prepared by a procedure as described in Scheme D, wherein all terms are as previously defined and the term "4—MeO—ϕ—" refers to a 4-methoxyphenyl group.

SCHEME D

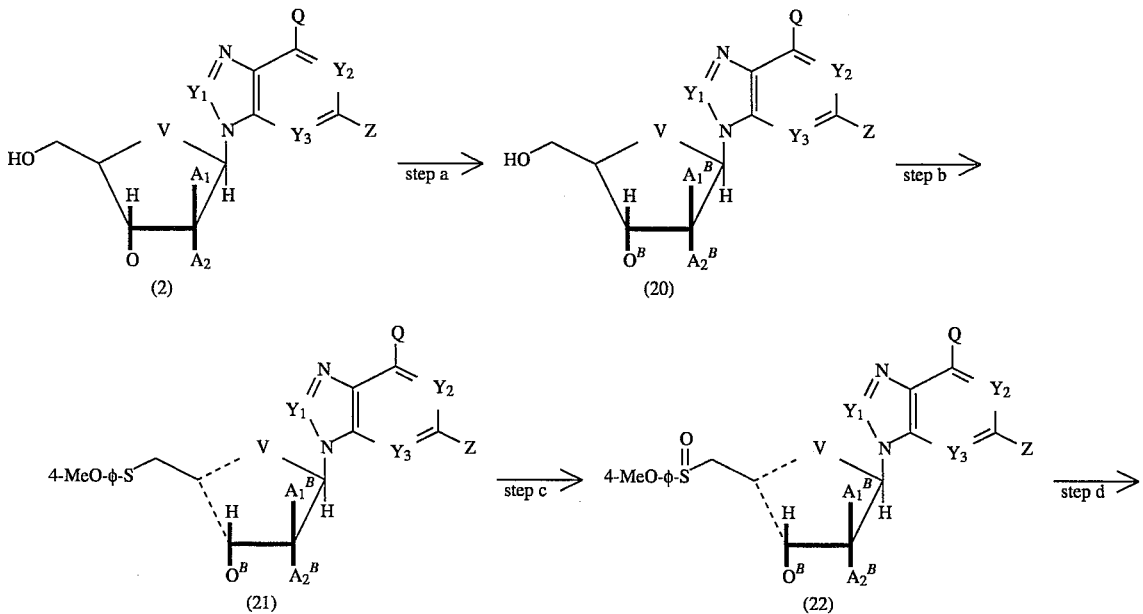

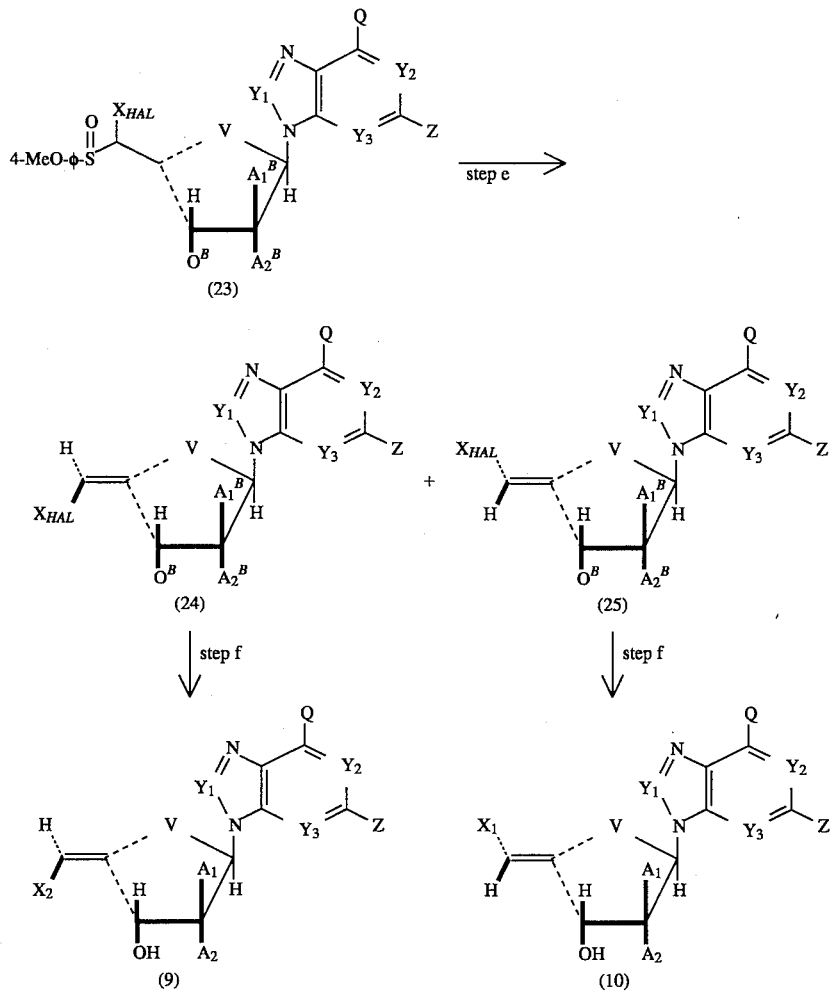

In step a, reactive hydroxy groups of the appropriate derivative (2), other than the 5'-hydroxy, are blocked utilizing standard blocking agents well known in the art as described for Scheme A. Where $A_2$ is hydroxy, it is preferred to block the 2'- and 3'-hydroxy groups with a 2', 3'-O-isopropylidene blocking group. Where $A_2$ is not hydroxy, it is preferred to block the 3'-hydroxy and any 2'-hydroxy (wherein $A_1$ is hydroxy) with a benzoyl group. Where a 2', 3'-O-isopropylidene blocking group is not utilized, it is preferred to block the 3'-hydroxy and any 2'-hydroxy (wherein $A_1$ is hydroxy) after the reaction described in step b.

In step b, the 5'-hydroxy of the appropriately blocked 5'-hydroxy derivative (20) is subjected to a substitution reaction in which an alkyl-thio group replaces the 5'-hydroxy group to form the corresponding sulfide (21). The preferred sulfide is the 4-methoxyphenylsulfide which can be formed by reacting the appropriately blocked 5'-hydroxy derivative (20) with 4-methoxyphenyl disulfide in the presence of tributylphosphine.

In step c, the sulfide (21) is oxidized to the corresponding sulfinyl derivative (22) utilizing standard oxidizing agents well known and appreciated in the art such as 3-chloroperbenzoic acid.

In step d, the 5'-carbon of the sulfinyl derivative (22) is halogenated using a halogenating agent, such as the fluorinating agent diethylaminosulfur trifluoride (DAST), or the chlorinating agent sulfuryl chloride in the presence of a base such as pyridine, to yield the corresponding 5'-halo-sulfinyl derivative (23). The preferred fluorinating agent is DAST and the preferred chlorinating agent is sulfuryl chloride. Where DAST is utilized as the fluorinating agent, the fluorinated product must be re-oxidized after treatment with DAST with an equimolar amount of an oxidizing agent, such as 3-chloroperbenzoic acid, in order to provide the 5'-halo-sulfinyl derivative (23).

In step e, the sulfinyl group is then eliminated to yield the appropriately blocked 4'-vinylhalo derivatives (24 and 25) by heating the 5'-halo-sulfinyl derivative (23) in the presence of a base such as diisopropylethyl amine.

In step f, the blocking groups of the appropriately blocked 4'-vinylhalo derivatives (24 and 25) are removed according to conventional procedures and techniques well known and appreciated in the art such as those described for Scheme A. The (Z) and (E) isomers of the 4'-vinylhaloaristeromycin/adenosine derivative, i.e., (9) and (10), are thus formed. These isomers can be separated by conventional resolution techniques well known and appreciated in the art.

The present invention provides a method of effecting immunosuppression, and more specifically, a method of suppressing cell-mediated immunity, in a patient in need thereof comprising administering to said patient an effective immunosuppressive amount of a compound of formula (1).

As used herein, the term "patient" refers to a warm-blooded animal such as a mammal which is suffering from a disease, such as an autoimmune disease or "graft versus host" disease, or is in danger of rejection of a transplanted allogeneic tissue or organ. It is understood that humans, mice and rats are included within the scope of the term "patient".

Administration of a compound of formula (1) to a patient results in an immunosuppressive effect in the patient. More specifically, administration of a compound of formula (1) to a patient results in suppression of cell-mediated immunity in the patient. In other words, by treatment of a patient with a compound of formula (1), the adaptive immune response of the patient and, more specifically, the cell-mediated adaptive immune response in the patient, is inhibited or suppressed over that present in the absence of treatment.

A patient is in need of treatment with an immunosuppressive agent, such as a compound of formula (1), where the patient is suffering from an autoimmune disease, "graft versus host" disease or in order to prevent rejection of transplanted allogeneic tissues or organs. The term "autoimmune disease" refers to those disease states and conditions wherein the immune response of the patient is directed against the patient's own constituents resulting in an undesireable and often terribly debilitating condition.

Patients suffering from autoimmune diseases such as rheumatoid arthritis, insulin-dependent diabetes mellitus, certain hemolytic anemias, rheumatic fever, thyroiditis, ulceractive colitis, myestheniagravis, glomerulonephritis, allergic encephalo-myelitis, continuing nerve and liver destruction which sometimes follows vital hepatitis, multiple sclerosis and systemic lupus erythematosus are in need of treatment with an immunosuppressive agent such as a compound of formula (1). Rheumatoid arthritis, insulin-dependent diabetes mellitus and multiple sclerosis are characterized as being the result of a cell-mediated autoimmune response and appear to be due to the action of T-cells. As such, treatment of patients suffering from these diseases by administration of a compound of formula (1) will be particularly effective in preventing further deterioration or worsening of the patient's condition. Treatment of a patient at an early stage of an autoimmune disease, such as rheumatoid arthritis, insulin-dependent diabetes mellitus or multiple sclerosis, would be particularly effective in preventing further deterioration of the disease state into a more serious condition. For example, insulin-dependent diabetes mellitus (IDDM) is an autoimmune disease which is believed to result from the autoimmune response directed against the β-cells of the islets of Langerhans which secrete insulin. Treatment of a patient suffering from an early stage of IDDM prior to the complete destruction of the β-cells of the islets of Langerhans would be particularly useful in preventing further progression of the disease since it would prevent or inhibit further destruction of remaining insulin-secreting β-cells. It is understood that treatment of a patient suffering from an early stage of other autoimmune diseases will also be particularly useful to prevent or inhibit further natural progression of the disease state to more serious stages.

Patients who have received or who are about to receive an allogeneic tissue or organ transplant, such as an allogeneic kidney, liver, heart, skin, bone marrow, are also patients who are in need of prophylactic treatment with an immunosuppressive agent such as a compound of formula (1). An immunosuppressive agent will prevent the cell-mediated immune response of the donee from rejecting the allogeneic tissue or organ of the donor. Likewise, patients suffering from "graft versus host" disease are patients who are in need of treatment with an immunosuppressive agent such as a compound of formula (1). An immunosuppressive agent will prevent the cell-mediated immune response of the transplanted tissue or organ from rejecting the allogeneic tissue or organ of the donee.

Based on standard clinical and laboratory tests and procedures, an attending diagnostician, as a person skilled in the art, can readily identify those patients who are in need of treatment with an immunosuppressive agent such as a compound of formula ( 1 ).

An effective immunosuppressive amount of a compound of formula (1) is that amount which is effective, upon single or multiple dose administration to a patient, in providing an immunosuppressive effect or, more particularly, a cell-mediated immunosuppressive effect. An immunosuppressive effect refers to the slowing, interrupting, inhibiting or preventing the further expression of the immune response or of the cell-mediated immune response.

An effective immunosuppressive amount of a compound of formula (1) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective immunosuppressive amount of a compound of formula (1) is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient, a compound of formula (1) can be administered in any form or mode which makes the compound bioavailable in effective amounts, including oral and parenteral routes. For example, compounds of formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of formula (1), while effective themselves, may be formulated and administered in the form of their pharmaceutically acceptable acid addition salts for purposes of stability, convenience of crystallization, increased solubility and the like..

A compound of formula (1) may be administered in the form of a pharmaceutical composition comprising an effective immunosuppressive amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, PRIMOGEL®, corn starch and the like; lubricants such as magnesium stearate or STEROTEX®; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of formula (1) may be incorporated into a solution or suspension. These preparations should contain at least 0.1% of a compound of the invention, but may be varied to be between 0.1 and about 50% of the weight thereof. The amount of the compound present in such compositions should be such that a suitable dosage will be obtained. Preferred compositions and preparations are prepared so that a parenteral dosage unit contains between 5.0 to 100 milligrams of the compound of formula (1).

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of the formula (1) in the method of use of the present invention.

With respect to the substituents $X_1$ and $X_2$, compounds wherein one of $X_1$ and $X_2$ is fluorine and the other is hydrogen are generally preferred. Compounds wherein $X_1$ is fluorine and $X_2$ is hydrogen are especially preferred.

With respect to the substituents $A_1$ and $A_2$, compounds wherein one of $A_1$ and $A_2$ is hydroxy and the other is hydrogen are generally preferred. Compounds wherein $A_1$ is hydrogen and $A_2$ is hydroxy are especially preferred.

The following are additional preferred embodiments: compounds wherein V is oxy, compounds wherein $Y_1$ is a CH group, compounds wherein $Y_2$ is nitrogen, compounds wherein $Y_3$ is nitrogen and compounds wherein Z is hydrogen.

Finally, with respect to Q, those compounds wherein Q is $NH_2$ or $NHCH_3$ are generally preferred with those wherein Q is $NH_2$ being especially preferred.

The following list identifies compounds of the formula (1) which are particularly preferred embodiments of the present invention:

(Z)-4',5'-didehydro-5'-deoxy-5'-fluoroadenosine
4',5'-didehydro-5'-deoxy-2,5'-difluoroadenosine
(Z)-9(5-deoxy-5-fluoro-β-D-threo-pent-4-enofuranosyl)-9H-purin- 6-amine
[1R-(α, 2α, 3β, 5E)-3-(4-amino-1H-imidazo[4,5-c]pyridin-1-yl)- 5-(fluoromethylene-1,2-cyclopentanediol
(Z)-1-(5-deoxy-5-fluoro-β-D-erythro-pent-4-enofuranosyl)-1H-imidazo[4,5-c]pyridin-4-amine
[1R-(1α, 2α, 3β, 5E)]-3-1(6-amino-9H-purin-9-yl)- 5(fluoromethylene)-1,2-cyclopentanediol
(Z)-4',5'-didehydro-2',5'-dideoxy-5'-fluoroadenosine
4',5'-didehydro-5'-deoxy-5',5'-difluoroadenosine
4',5'-didehydro-5'-deoxy-2,5'- 5'-trifluoroadenosine
9(5-deoxy-5,5-difluoro-β-D-threo-pent-4-enofuranosyl)-9H-purin- 6-amine
[1R-(1α, 2α, 3β)-3-(4-amino-1H-imidazo[4,5-c]pyridin-1-yl)- 5-difluoromethylene)-1,2-cyclopentanediol
1-(5-deoxy-5,5-difluoro-β-D-erythro-pent-4-enofuranosyl)-1H-imidazo[4,5-c]pyridin-4-amine
[1R-(1α, 2α, 3β)]-3-(6-amino-9H-purin-9-yl)-5-(difluoromethylene)- 1,2-cyclopentanediol
4',5'-didehydro-2',5'-dideoxy-5,5'-difluoroadenosine The following example illustrates the method of use of the compounds of formula (1) according to the present invention. This example is understood to be illustrative only and is not intended to limit the scope of the invention in any way. As used herein the following terms have the indicated meanings: "μM" refers to micromolar concentration; "mM" refers to millimolar concentration; "M" refers to molar concentration; "S.D." refers to standard deviation; "μg" refers to micrograms; "μL" refers to microliters; "i.p." refers to intraperitoneal; "ELISA" refers to Enzyme-linked Immunosorbant Assay; "Dulbecco's PBS" refers to phosphate buffered saline; "RPMI 1640" refers to Roswell Park Memorial Institute medium 1640; "FCS" refers to fetal calf serum; "HEPES buffer" refers to N-[2-hydroxyethyl]piperazine-N'-[2-ethanesulfonic acid] buffer; "CM" refers to culture medium; "μCi" refers to microCurie; "cpm" refers to counts per minute.

EXAMPLE 4

EFFECT OF (Z)-4',5'-DIDEHYDRO-5'-DEOXY-5'-FLUOROADENOSINE ON MITOGEN STIMULATION OF HUMAN PERIPHERAL BLOOD MONONUCLEAR CELLS

Materials and Methods

Cells: Human peripheral blood mononuclear cells were isolated from samples of blood (in 0.01M sodium citrate) using 50 mL LEUKOPREP® separation tubes (Becton Dickenson, Lincoln Park, N.J.). Tubes were centrifuged at room temperature for 15 minutes at 2400 rpm in a swinging bucket rotor. The cells recovered at interface were washed in Dulbecco's PBS and resuspended in RPMI 1640 containing 10% FCS, $5 \times 10^{-5}$M 2-mercaptoethanol, 2 mM L-glutamine, 1% penicillin-streptomycin and 1 mM HEPES buffer (CM).

Mitogenic Assay: Human peripheral blood mononuclear cells ($2 \times 10^5$) were incubated with pokeweed mitogen at a final concentration of 0.1 µg/mL or Concanavalin A at a final concentration of 1.0 µg/mL in 96 well flat-bottomed microtiter plates (Falcon 3072, Becton Dickinson). Compounds to be tested were added at the initiation of culture. The final volume was 0.2 mL. The cultures were incubated in 95% humidified air/5% $CO_2$ at 37° C. for 2 days (Concanavalin A) or 6 days (Pokeweed mitogen). Eighteen hours before termination of the cultures, each well was pulsed with 1 µCi of [$^3$H]-thymidine. Cells from individual wells were harvested onto glass fiber filter paper with an automated multi-sample harvester. Filters were placed in scintillation fluid (Universal Cocktail, ICN Radiochemicals, Irvin, Calif.) and the [$^3$H]-thymidine incorporation, in counts per minute (cpm), was measured in a Packard Tri-carb 4640 Scintillation Counter.

Peripheral blood mononuclear cells from three individuals were cultured with an optimal concentration of pokeweed mitogen, a T-dependent B-cell mitogen, in the presence of increasing concentrations of (Z)-4',5'-didehydro- 5'-deoxy-5'-fluoroadenosine. As shown in Table 1, (Z)-4',5'-didehydro-5'-deoxy-5'-fluoroadenosine produced a dose dependent inhibition of pokeweed stimulated proliferation of human peripheral blood mononuclear cells with an $IC_{50}$ of 0.84 µM. Similar studies were performed culturing human peripheral blood cells with an optimal concentration of Concanavalin A, a potent T-cell mitogen. As shown in Table 1, (Z)-4',5'-didehydro-5'-deoxy-5'-fluoroadenosine produced a dose dependent inhibition of Concanavalin A stimulated proliferation of human peripheral blood mononuclear cells with an $IC_{50}$ of 0.25 µM.

TABLE 1

EFFECT OF (Z)-4',5'-DIDEHYDRO-5'-DEOXY-5'-FLUOROADENOSINE ON MITOGEN STIMULATION OF HUMAN PERIPHERAL BLOOD MONONUCLEAR CELLS

| Concentration of Compound A (µM) | Proliferation (% of Control) Pokeweed mitogen | Proliferation (% of Control) Concanavalin A mitogen |
| --- | --- | --- |
| 0 (Control) | 100 | 100 |
| .001 | 97.4 | 100.2 |
| .01 | 103.3 | 100.7 |
| .1 | 72.1 | 66.4 |
| 1.0 | 50.9 | 15.8 |
| 10.0 | 19.7 | 3.7 |
| $IC_{50}$ | 0.84µM | 0.25µM |

TABLE 1-continued

EFFECT OF (Z)-4',5'-DIDEHYDRO-5'-DEOXY-5'-FLUOROADENOSINE ON MITOGEN STIMULATION OF HUMAN PERIPHERAL BLOOD MONONUCLEAR CELLS

| Concentration of Compound A (µM) | Proliferation (% of Control) Pokeweed mitogen | Proliferation (% of Control) Concanavalin A mitogen |
| --- | --- | --- |

Compound A = (Z)-4',5'-didehydro-5'-deoxy-5'-fluoroadenosine

EXAMPLE 5

EFFECT OF (Z)-4',6'-DIDEHYDRO-5'-DEOXY-5'-FLUOROADENOSINE ON MITOGEN STIMULATION OF MURINE MONONUCLEAR CELLS

Materials and Methods

Cells: Spleens and/or lymph nodes from a total of 16 individual outbred CD-1 mice (Charles River, Wilmington, Mass.) were asceptically removed, pooled, and single cell suspensions were made in Hank's Balanced Salt Solution (HBSS, calcium and magnesium free). Erythrocytes were lysed by treatment with Tris-buffered ammonium chloride (0.155M $NH_4Cl$, 0.0165M Tris, pH 7.2). Mononuclear cells were washed with HBSS and resuspended in Dulbecco's PBS and resuspended in RPMI 1640 containing 10% FCS, 5×10–5 M 2mercaptoethanol, 2 mM L-glutamine, 1% penicillin-streptomycin and 1 mM HEPES buffer (CM).

Mitogenic Assay: Murine splenic mononuclear cells ($5 \times 10^5$) were incubated with Concanavalin A at a final concentration of 2.5 µg/mL in 96 well flat-bottomed microtiter plates. Compounds to be tested were added at the initiation of culture. The final volume was 0.2 mL. The cultures were incubated in 95% humidified air/5% $CO_2$ at 37° C. for 2 days. Eighteen hours before termination of the cultures, each well was pulsed with 1 µCi of [$^3$H]-thymidine. Cells from individual wells were harvested onto glass fiber filter paper with an automated multi-sample harvester. Filters were placed in scintillation fluid (Universal Cocktail, ICN Radiochemicals, Irvin, Calif.) and the [$^3$H]-thymidine incorporation, in counts per minute (cpm), was measured in a Packard Tri-carb 4640 Scintillation Counter.

Murine splenic mononuclear cells were were cultured with Concanavalin A, a T-cell mitogen, in the presence of increasing concentrations of (Z)-4',5'-didehydro-5'-deoxy-5'-fluoroadenosine As shown in Table 2, (Z)-4',5'-didehydro-5'-deoxy-5'-fluoroadenosine produced a dose dependent inhibition of Concanavalin A stimulated proliferation of murine splenic mononuclear cells with an $IC_{50}$ of 0.19 µM.

TABLE 2

EFFECT OF (Z)-4',5'-DIDEHYDRO-5'-DEOXY-5'-FLUOROADENOSINE ON MITOGEN STIMULATION OF MURINE SPLENIC MONONUCLEAR CELLS

| Concentration of Compound A (µM) | Proliferation (% of Control) Concanavalin A mitogen |
| --- | --- |
| 0 (Control) | 100 |
| .001 | 96.3 |
| .01 | 86.0 |

TABLE 2-continued

EFFECT OF (Z)-4',5'-DIDEHYDRO-5'-DEOXY-5'-FLUOROADENOSINE ON MITOGEN STIMULATION OF MURINE SPLENIC MONONUCLEAR CELLS

| Concentration of Compound A ($\mu$M) | Proliferation (% of Control) Concanavalin A mitogen |
|---|---|
| .1 | 51.8 |
| 1.0 | 28.6 |
| 10.0 | 17.9 |
| $IC_{50}$ | 0.19$\mu$M |

Compound A = (Z)-4',5'-didehydro-5'-deoxy-5'-fluoroadenosine

EXAMPLE 6

EFFECT OF (Z)-4',5'-DIDEHYDRO-5'-DEOXY-5'-FLUOROADENOSINE ON STIMULATION OF IMMUNE RESPONSE BY T-DEPENDENT ANTIGEN in vivo

Materials and Methods

In vivo immune response: Mice were radomly distributed by weight into 3 groups of ten. Dosing i.p. with Dulbecco's phosphate buffered saline (PBS) or (Z)-4',5'-didehydro-5'-deoxy- 5'-fluoroadenosine (at 5 or 10 mg/Kg) dissolved in PBS was begun one day prior to immunization. Ovalbumin (Sigma, St. Louis, Mo.) at 2 mg/mL in PBS was emulsified in an equal volume of Freunds complete adjuvant and 50 $\mu$L, containing 50 $\mu$g ovalbumin, was injected into each footpad. Animals were dosed daily. Ten days after the immunization, the animals were bled for serum and sacrificed. Serum levels of anti-ovalbumin IgG were quantitated in an ELISA. Specifically, 100 $\mu$L of a 1% ovalbumin solution in Tris-buffered saline (TBS) (20 mM Tris, 500 mM NaCl, pH 7.5) was added to individual wells of a 96 well ELISA microtiter plate. The plate was incubated for 2 hours at room temperature and the wells were washed 3 times with TBS containing 0.05% Tween 20 (TBS-Tween). Dilutions of the serum samples in TBS-Tween (100 $\mu$L) were added to the wells, which were then incubated for one hour at room temperature. The plate was again washed 3 times with TBS-Tween. The wells were then incubated with 100 $\mu$L of a 1:1000 dilution of rabbit anti-mouse IgG labled with horse radish peroxidase (Bio-Rad, Richmond, Calif.) for one hour at room temperature. After washing 3 times with TBS-Tween, the wells were incubated with 100 $\mu$L of Bio-Rad peroxidase substrate [2,2'-azino-di-(3-ethyl-benzthiazoline sulfonate) in cocodylic acid buffer and hydrogen peroxide]. Absorbance at 405 nm was measured and the antibody titer was calculated from the linear regression curve of each serum sample and is reported as the log of the dilution which gave an absorbance reading of 0.750, unless otherwise indicated.

As shown in Table 3, treatment of mice with (Z)-4',5'-didehydro- 5'-deoxy-5'-fluoroadenosine at 5 or 10 mg/Kg significantly reduced the serum levels of anti-ovalbumin IgG compared to Controls.

TABLE 3

EFFECT OF (Z)-4',5'-DIDEHYDRO-5'-DEOXY-5'-FLUOROADENOSINE ON STIMULATION OF IMMUNE RESPONSE BY T-DEPENDENT ANTIGEN in vivo

| Dose of Compound A (mg/Kg) | Anti-Ovalbumin Titer ± S.D. (range) |
|---|---|
| 0 (Control) | 1880 ± 1083 |
|  | 2593 ± 2133 |
|  | (936–8005) |
| 5 | 550 ± 272 |
|  | (210–998) |
| 10 | 375 ± 124 |
|  | (198–619) |

Compound A = (Z)-4',5'-didehydro-5'-deoxy-5'-fluoroadenosine

What is claimed is:

1. A method of effecting immunosuppression in a patient in need thereof comprising administering to said patient an effective immunosuppressive amount of a compound of the formula

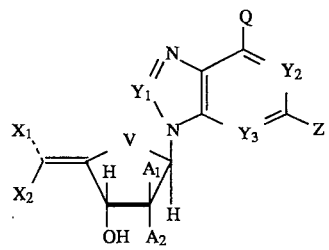

wherein

V is oxy or methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a $CNH_2$ group, $Y_2$ and $Y_3$ are each independently nitrogen or a CH group, Q is $NH_2$, NHOH, $NHCH_3$, or hydrogen, and Z is hydrogen, halogen, or $NH_2$.

2. A method according to claim 1 wherein the patient is in need of treatment for allograft rejection.

3. A method according to claim 1 wherein the patient is in need of treatment for an autoimmune disease.

4. A method according to claim 3 wherein the autoimmune disease is insulin-dependent diabetes mellitus.

5. A method according to claim 3 wherein the autoimmune disease is multiple sclerosis.

6. A method according to claim 3 wherein the autoimmune disease is rheumatoid arthritis.

7. A method according to claim 1 wherein the compound is 4',5'-didehydro-5'-deoxy-5'-fluoroadenosine.

8. A method according to claim 1 wherein the compound is ( Z ) -4',5'-didehydro-5'-deoxy-5'-fluoroadenosine.

* * * * *

UNITED STATES PATENT AND TRADEMARK OFFICE
CERTIFICATE OF CORRECTION

PATENT NO. : 5,470,837
DATED : November 28, 1995
INVENTOR(S) : Jeffrey A. Wolos, et. al.

It is certified that error appears in the above-indentified patent and that said Letters Patent is hereby corrected as shown below:

Column 4, Line 24 patent reads: "an autoimmune diseases" and should read -- autoimmune disease --.
Column 5, Line 24 patent reads: "CNH2" and should read -- $CNH_2$ --.
Column 5, Line 40 patent reads: "(1)" and should read -- (2) --.
Column 8, Line 56 patent reads: "art For" and should read -- art. For --.
Column 9, Line 51 patent reads: "N6-" and should read -- $N^6$- -- .
Column 12, Line 66 patent reads: "4α)" and should read -- 4β) -- .
Column 13, Line 12 patent reads: "2α," and should read -- 2β, -- .
Column 13, Line 7 patent reads: "2α," and should read -- 2β, -- .

The structure (11) in SCHEME B shows at Column 13, approximately Line 30: "  " and should read -- 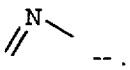 -- .

Column 16, Line 26 patent reads: " -5', 6' " and should read -- -5', 5' --.
Column 16, Line 29 patent reads: "1, α2E," and should read -- 1α, 2E, --.
Column 16, Line 36 patent reads: "4,β" and should read -- 4β -- .
Column 19, Line 10 patent reads: " -5', 6' " and should read -- -5', 5' -- .
Column 24, Line 62 patent reads: "like.." and should read -- like.-- .

UNITED STATES PATENT AND TRADEMARK OFFICE
CERTIFICATE OF CORRECTION

PATENT NO. : 5,470,837
DATED : November 28, 1995
INVENTOR(S) : Jeffrey A. Wolos, et. al.

It is certified that error appears in the above-indentified patent and that said Letters Patent is hereby corrected as shown below:

Column 28, Line 15 patent reads: " 4', 6' " and should read -- 4', 5' -- .
Column 28, Line 31 patent reads: "5x10-5 M 2mercaptoethanol" and should read -- $5 \times 10^{-5}$ M 2-mercaptoethanol -- .
Column 28, Line 48 patent reads: "were were" and should read -- were -- .

Signed and Sealed this

Eighteenth Day of February, 1997

Attest:

BRUCE LEHMAN

Attesting Officer

Commissioner of Patents and Trademarks